(12) United States Patent
Wong et al.

(10) Patent No.: US 9,636,089 B2
(45) Date of Patent: May 2, 2017

(54) FLUID SPECIMEN COLLECTION DEVICE

(71) Applicant: BRANAN MEDICAL CORPORATION, Irvine, CA (US)

(72) Inventors: Raphael Wong, Irvine, CA (US); Kerkong Tung, Del Mar, CA (US); Wen Li, Los Angeles, CA (US)

( * ) Notice: Subject to any disclaimer, the term of this patent is extended or adjusted under 35 U.S.C. 154(b) by 0 days.

(21) Appl. No.: 14/289,146

(22) Filed: May 28, 2014

(65) Prior Publication Data

US 2014/0271367 A1 Sep. 18, 2014

Related U.S. Application Data

(63) Continuation of application No. 12/854,812, filed on Aug. 11, 2010, now Pat. No. 8,771,607.

(60) Provisional application No. 61/235,281, filed on Aug. 19, 2009.

(51) Int. Cl.
*A61B 10/00* (2006.01)

(52) U.S. Cl.
CPC ........ *A61B 10/007* (2013.01); *A61B 10/0096* (2013.01); *A61B 2010/0006* (2013.01); *A61B 2010/0009* (2013.01)

(58) Field of Classification Search
CPC .............. A61B 10/007; A61B 2010/06; A61B 2010/09; A61B 10/96
See application file for complete search history.

(56) References Cited

U.S. PATENT DOCUMENTS

| 6,277,646 | B1 | 8/2001 | Guirguis |
| 7,981,382 | B2 * | 7/2011 | Wong et al. ............... 422/401 |
| 2003/0021726 | A1 * | 1/2003 | Wu et al. ................. 422/58 |
| 2006/0280650 | A1 * | 12/2006 | Wong et al. .............. 422/58 |
| 2011/0044856 | A1 * | 2/2011 | Wong et al. .............. 422/69 |

OTHER PUBLICATIONS

Extended European Search Report dated Jan. 23, 2015 for Corresponding European Patent Application No. 10810410.0, filed Feb. 24, 2012.

* cited by examiner

*Primary Examiner* — Sam P Siefke
(74) *Attorney, Agent, or Firm* — Innovation Capital Law Group, LLP; Vic Lin (57) ABSTRACT

A drug test device for bodily fluids, such as urine, includes a cup and a removable lid which houses one or more test strips. The lid is releasably locked onto the cup so as to align dipping ends of the test strips exposed through an underside of the lid with a position stabilizer, thereby causing the dipping ends to be located downwardly and submerged in fluid when the device is placed on its side in a reactive position. The position stabilizer may comprise a sidewall indentation that reduces the internal volume of the cup and keeps the cup from rolling when placed on its side.

17 Claims, 8 Drawing Sheets

FLUID SPECIMEN COLLECTION DEVICE

RELATED APPLICATIONS

This application is a continuation of patent application Ser. No. 12/854,812 filed on Aug. 11, 2010 and entitled FLUID SPECIMEN COLLECTION DEVICE and claims priority from U.S. Provisional Patent Application Ser. No. 61/235,281 filed on Aug. 19, 2009 and entitled FLUID SPECIMEN COLLECTION DEVICE, the disclosures of which are incorporated herein by reference in their entirety.

BACKGROUND OF THE INVENTION

1. Field of the Invention

The present invention relates generally to a fluid specimen collection device.

2. Description of Prior Art and Related Information

Drug testing typically requires collection of urine in a conventional cup. Fluid samples may then be transferred onto a test device. Such transfers leave the technician vulnerable to exposure and skin contact with the urine. Moreover, having to open the cup exposes the urine sample to potential contamination.

SUMMARY OF THE INVENTION

The present invention provides structures and methods which overcome the deficiencies in the prior art.

In one aspect, a fluid collection device is provided. The device comprises a cup defining a reservoir and comprising a sidewall having a position stabilizer. The position stabilizer is configured to prevent the cup from rolling when the cup is titled to rest the stabilizer against a generally horizontal surface. A lid is removably coupled to the cup. The lid comprises a test strip and an opening accessible to the test strip. The opening is located adjacent a tilt portion of a periphery of the lid. The lid is rotatable with respect to the cup to facilitate fluid communication between the cup and the test strip. The lid is configured to be releasably locked in a fixed position such that the tilt portion of the periphery is aligned with the position stabilizer to direct fluid within the cup towards the opening in the lid. The device further comprises a releasable lock to temporarily lock the lid in the fixed position.

The position stabilizer preferably comprises an indentation. The indentation preferably defines a bottom width that is greater than a top width. The indentation may comprise a concave outer surface. The indentation may comprise a pair of axial ridges configured to abut the surface when the cup is tilted.

Each ridge has a bottom point such that the pair of bottom points define a line extending therebetween. An innermost point of a bottom of the indentation extends an inward distance from the line preferably in a range of 0.1 inch to 1 inch.

The lid may also comprise a lid position stabilizer configured to align with the position stabilizer when the lid is locked to the cup. The tilt portion of the periphery may comprise a flat surface.

In a further aspect, a fluid collection device comprises a cup configured to hold a sample fluid. A position stabilizer is configured to prevent the cup from rolling when the cup is tilted and resting on a generally horizontal surface. The position stabilizer comprises an indentation so as to form a pair of ridges configured to abut the generally horizontal surface. A lid is removably coupled to the cup. The lid comprises a test strip and an opening accessible to the test strip. The lid is rotatable with respect to the cup to facilitate fluid communication between the cup and the test strip.

The position stabilizer may be integral with the cup.

In another preferred embodiment, the cup may comprise a first cup, and the position stabilizer is included in a second outer cup configured to receive the first cup.

The device further comprises a releasable lock to temporarily lock the lid in a fixed position with respect to the cup where the opening in the lid is aligned with the position stabilizer to facilitate flow of fluid into the lid when the cup is tilted and stabilized by the groove.

The cup preferably comprises a reduced internal volume configured to require less than a full reservoir of fluid in order to direct a sufficient amount of said fluid to the lid.

Each ridge has a bottom point, such that the pair of bottom points define a line extending therebetween. An innermost point of a bottom of the indentation preferably extends an inward distance from the line in a preferred range of 0.1 inch to 1 inch.

In a further aspect, a fluid collection device comprises a cup configured to hold a sample fluid. A position stabilizer is configured to prevent the cup from rolling when the cup is tilted and resting on a generally horizontal surface. The position stabilizer preferably comprises an indentation formed into a sidewall so as to form a pair of ridges configured to abut the generally horizontal surface. A lid is removably coupled to the cup. The lid comprises a test strip and an opening accessible to the test strip. The lid is configured to be releasably locked into a position with respect to the cup so as to align the opening with the position stabilizer.

Each ridge has a bottom point such that the pair of bottom points define a line extending therebetween. An innermost point of a bottom of the indentation extends an inward distance from the line in a preferred range of 0.1 inch to 1 inch.

The position stabilizer may be integral with the cup. In another preferred embodiment, the position stabilizer may be included in an add-on device, such as a second outer cup or a jacket with wrap-around bands.

In a further aspect, a drug test device for bodily fluids, such as urine, includes a cup and a removable lid which houses one or more test strips. The lid is releasably locked onto the cup so as to align dipping ends of the test strips exposed through an underside of the lid with a position stabilizer, thereby causing the dipping ends to be located downwardly and submerged in fluid when the device is placed on its side in a reactive position. The position stabilizer may comprise a sidewall indentation that reduces the internal volume of the cup and keeps the cup from rolling when placed on its side.

DETAILED DESCRIPTION OF THE PREFERRED EMBODIMENTS

The invention and its various embodiments can now be better understood by turning to the following detailed description wherein illustrated embodiments are described. It is to be expressly understood that the illustrated embodiments are set forth as examples and not by way of limitations on the invention as ultimately defined in the claims.

Figure 1:
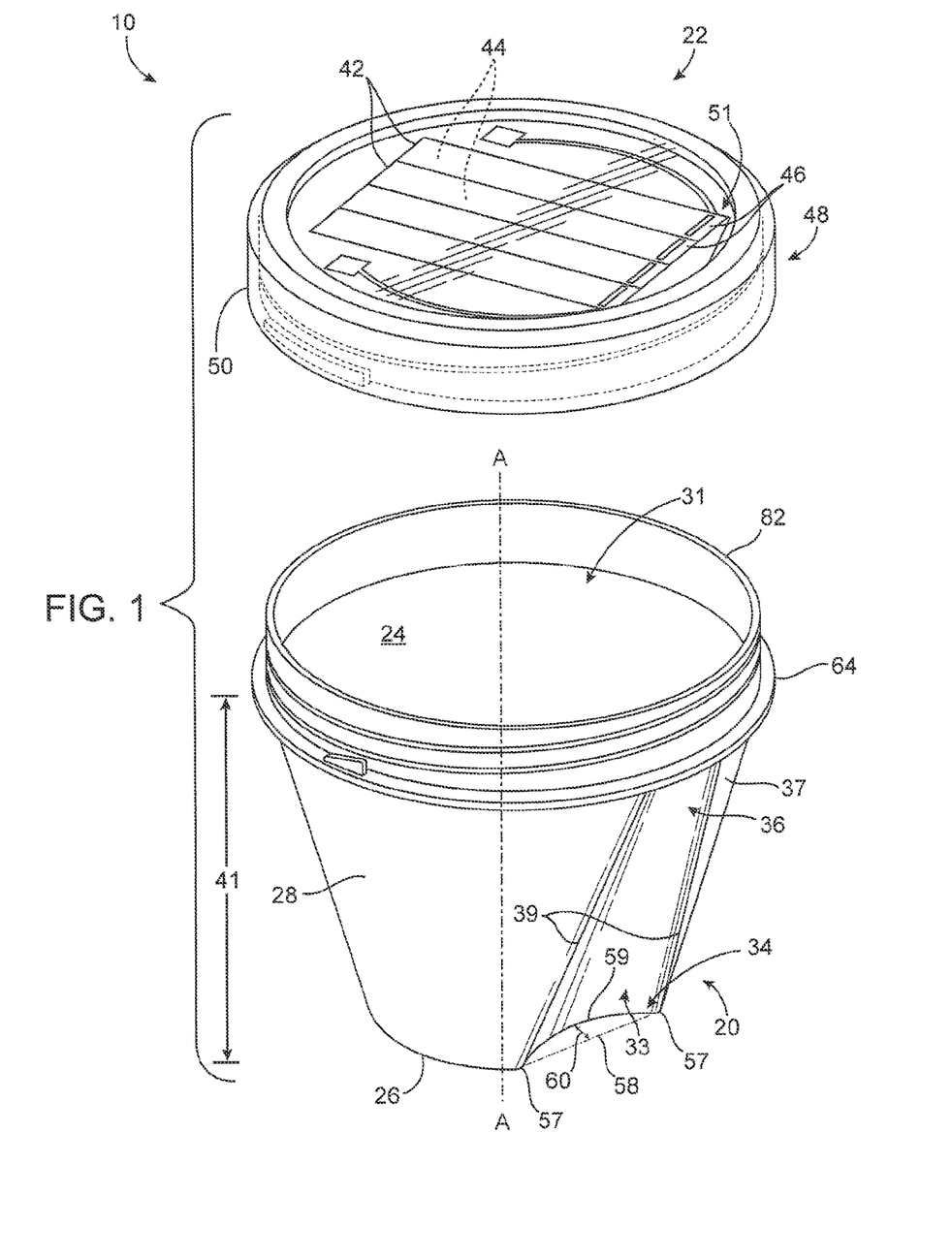
FIG. 1 is an exploded perspective view of a first preferred embodiment of a fluid specimen collection device.

A first preferred embodiment of a fluid specimen collection device is illustrated in FIG. 1 and designated generally by the reference numeral 10. The device 10 comprises a cup, or vessel, 20 and a removable lid, or cap, 22. The lid 22 is preferably rotatable with respect to the cup 20 and configured to be screwed onto the cup 20.

The cup 20 defines an axis "A" and an interior chamber, or reservoir, 24 for collecting and storing a fluid sample. The cup 20 comprises a bottom 26, a generally conical sidewall 28 and a top opening 31. The device 10 comprises a position stabilizer 33 which helps to keep the device 10 in a fixed position when the device 10 is tilted and resting against a generally horizontal surface. In particular, the position stabilizer 33 prevents the cup 20 from rolling when tilted.

The position stabilizer 33 may preferably be integral with or separate from the cup 20. In the first preferred embodiment, the position stabilizer 33 comprises an indentation 33 in the sidewall 28, and defines a resting side 36 of the device 10. The indentation 33 is concave with respect to the outer surface 37 of the sidewall 28 so as to form at least a pair of ridges 39 adapted to abut the horizontal surface on which the device 10 rests when tilted. Since the position stabilizer 33 is indented towards the reservoir 24, it will be appreciated that the stabilizer 33 also reduces the internal volume capacity of the reservoir 24, thereby reducing the amount of fluid necessary for collection in order to enable testing.

The bottom 26 is preferably circular except for indentation 33. As an example and not by way of limitation, the bottom 26 may have a radius of 0.5 inch to 1.5 inches.

Figure 2:
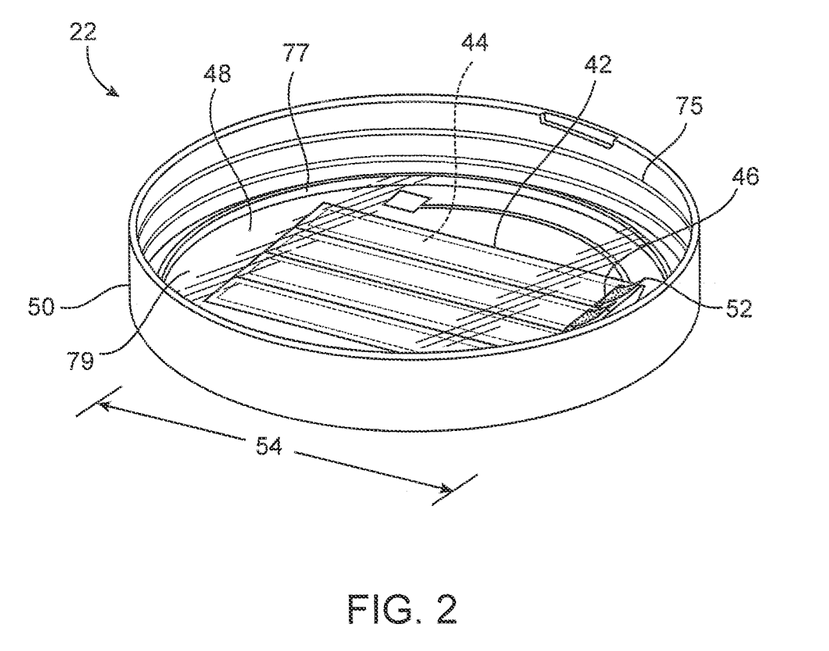
FIG. 2 is a perspective view of an underside of a lid of the first preferred embodiment.

In FIGS. 1 and 2, the lid 22 comprises one or more test chambers 42 for receiving test strips 44, including adulteration test strips. Each chamber 44 is in fluid communication with a corresponding port 46 opening from the bottom surface 48 of the lid 22. Since test strips 44 are typically elongate, the test chambers 42 may also be elongate in order to accommodate the test strips 44. The chambers 42 are configured in a substantially parallel array with the ports, or openings, 46 all disposed at one end adjacent to the tilt portion 48 of the lid periphery, or side rim 50. The tilt portion 48 of the lid periphery 50 comprises that portion of the rim 50, adjacent to the ports 46, which abuts or engages the horizontal surface when the lid 22 is locked into an operative position and the device 10 is tilted, as discussed more fully below. Thus, the lid 22 comprises a dipping region 51 where the ports 46 are arrayed.

Each test strip 44 is disposed in a chamber 42 with the initial, receiving end 52, or dipping end 52, protruding from the port 46 and downwardly toward the reservoir 24 of the cup 20. Thus, the length 54 of the chambers 42 are configured to be slightly shorter than the total length of the test strips 44 so to as to cause the dipping end 52 to protrude through the ports 46. Alternatively stated, the test strips 44 may be configured to be longer than the length 54 of the chambers 42 such that the dipping ends 52 extend through the ports 46 toward the reservoir 24.

In FIG. 1, it will be appreciated that the indentation 33 also comprises a carve-out that reduces the internal volume capacity of the 20. Where the lowest points 57 of the ridges 39 of the indentation 33 define a line 58 extending therebetween, the bottom of the indentation 33 in the preferred embodiment may comprise an innermost point 59 that is spaced an inward distance 60 from the line 58 in the preferred range of 0.1 inch to 1 inch in the first preferred embodiment. In this preferred embodiment, the indentation reduces internal volume preferably in the range of 4 ml to 14 ml than if the cup were configured without such an indentation.

In the first preferred embodiment, the indentation 33 comprises a wider bottom and a narrower top such that the indentation 33 is tapered as it extends upwardly. As an example and not by way of limitation, the bottom 34 of the indentation 33 may have a width in the preferred range of 0.5 inch to 2.5 inches, with an even more preferred range of 0.75 inch to 1.5 inches. The top 36 of the indentation 33 may have a width in the preferred range of 0.1 inch to 2 inches, with an even more preferred range of 0.25 inch to 1.25 inches. The cup 20 also defines a height 41 between the cup bottom 26 and where the cup 20 is configured to meet the lid 22, i.e., a the flange 64. As an example and not by way of limitation, this height 41 is approximately 2 inches to 3 inches in the preferred embodiment, but may vary in the preferred range of 1 inch to 5 inches.

Figure 3:
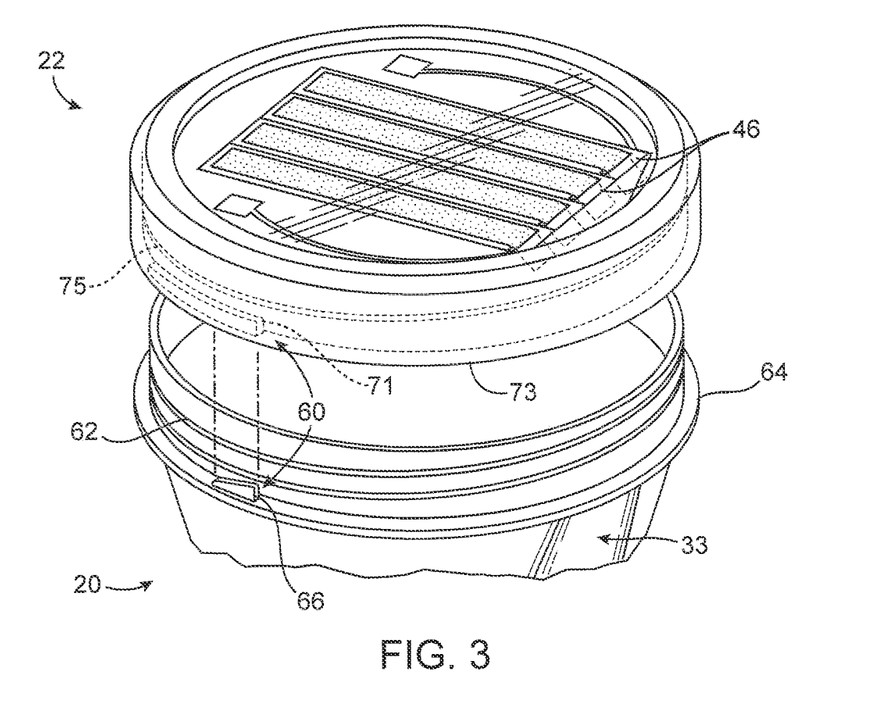
FIG. 3 is a close-up perspective view of the first preferred embodiment, with the lid and cup shown exploded.
Figure 4:
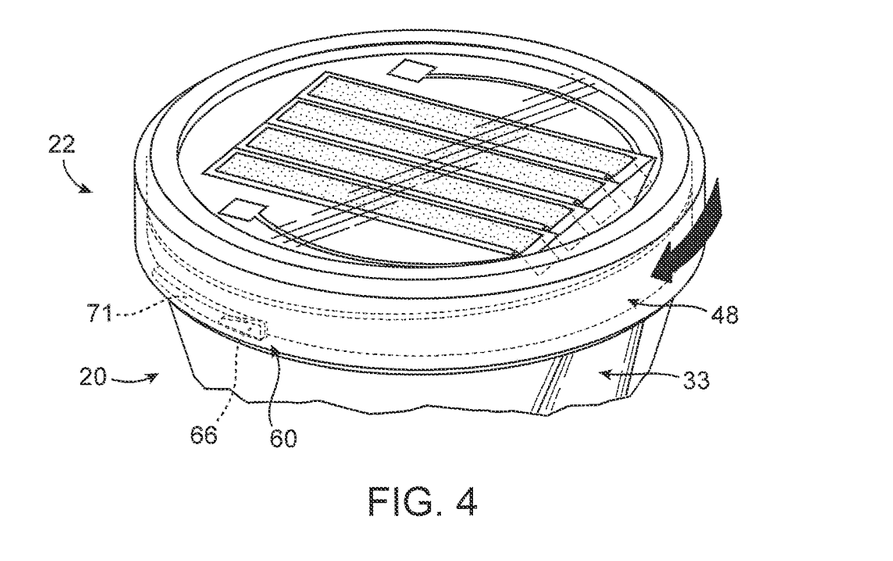
FIG. 4 is a close-up perspective view of the first preferred embodiment as assembled.

FIGS. 3 and 4 illustrate the operative connection between the lid 22 and the cup 20. In particular, FIG. 3 shows a lock mechanism 60 to releasably lock the lid 22 into a fixed position with respect to the cup 20 so as to align the ports 46 and corresponding dipping ends 52 with the position stabilizer 33.

The cup 20 comprises a top externally threaded portion 62 and an annular flange 64 located at the base of the externally threaded portion 64. In the preferred embodiment, the lock mechanism 60 comprises a detent, or ratchet, 66 disposed on a lid facing surface 68. The lock releasable lock mechanism 60 also comprises a corresponding groove 71 formed at a predetermined location along a bottom edge 73 of the lid rim 50 so as to receive and abut the detent 66.

In FIG. 3, the lid rim 50 also comprises an internally threaded portion 75 configured to mate with the externally threaded cup portion 62. An annular recess 77 may be formed on the underside of a top planar portion 79 of the lid 22 to help form a seal with a top edge 82 of the cup 20, shown in FIG. 1.

When the lid 22 is screwed onto the cup 20 as shown in FIG. 4, the detent 66 is received in the groove 71 and forms a stop guide to cease further rotation of the lid. As a result, the lid tilt portion 48 is aligned with the position stabilizer 33.

While the preferred embodiment of the device 10 above comprises a threaded connection between the cup 20 and lid 22 where the lid 22 is screwed onto the cup 20, it is to be expressly understood that a variety of different mechanisms may be employed to removably secure the lid 22 to the cup 20.

Figure 5:
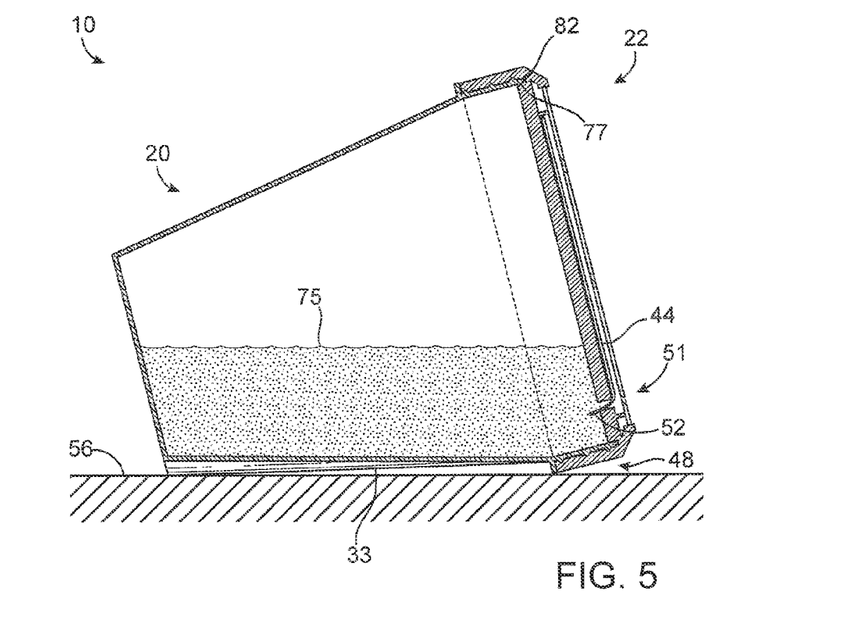
FIG. 5 is an axial cross-sectional view of the first preferred embodiment in a reactive position, as tilted and resting on a generally horizontal surface.

FIG. 5 is a cross-sectional, operative view of the preferred embodiment of the device 10 when tilted and resting on a generally horizontal surface 56. In this testing or reactive position, sample fluid 75 within the device 10 is directed towards the lid 22. Since the dipping ends 52 of the test strips 44 are disposed adjacent to the tilt portion 48 of the lid 22, these protruding ends 52 are thus positioned near the bottom of the device 10 when tilted, namely, adjacent to the horizontal surface 56, thereby facilitating contact with the fluid 75.

When the preferred device 10 is tilted and resting on the horizontal surface 56, the position stabilizer 33 keeps the device 10 from rolling, and thus maintains the dipping region 51 of the lid 22 at the bottom towards which the fluid within the device 10 can gravitate. As shown in FIG. 5, the dipping end 52 of the test strip 44 remains submerged in the fluid 75 when the cup 20 is held steady by the position stabilizer 33, this position facilitated by the locking of lid 22 to the cup 20 at a precise location where the lid tilt portion 48 is releasably locked adjacent to the position stabilizer 33.

FIG. 5 also illustrates the annular recess 77 in the underside of the lid 22 that forms a seal with the top edge 82 of the cup 20. This seal formed between the lid 22 and cup 20 prevents spillage as the cup is tilted in this operative, testing position. As a result, the technician never has to come into contact with the urine to perform the testing.

Figure 6:
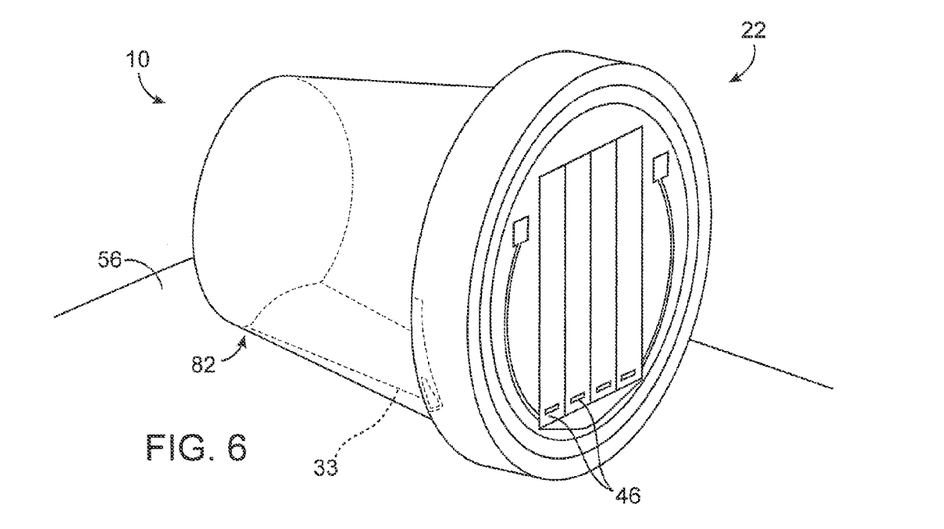
FIG. 6 is a front perspective view of a first preferred embodiment in the reactive position.

For purposes of clarity, FIG. 6 shows the device 10 laid on its side against a horizontal surface 56. In this tilted testing position, the position stabilizer 33 keeps the 10 from rolling. With the lid 22 releasably locked into position with the cup 20 such that the ports 46 are located downwardly, adjacent to the stabilizer 33, the dipping ends of the strips (not shown) are thus positioned to receive the fluid being directed towards the lid by virtue of gravity.

Figure 7:
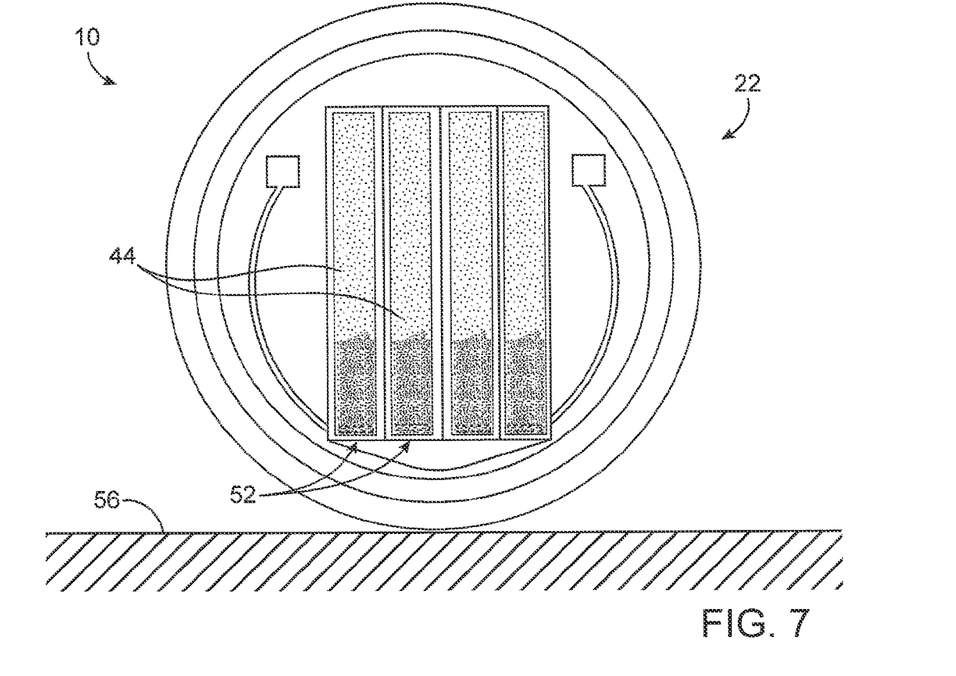
FIG. 7 is a front view of the first preferred embodiment in a reactive position.

FIG. 7 is an operative, front view of the device 10 in the reactive testing position shown in FIG. 6, namely with the position stabilizer maintaining the device 10 in a stable, fixed position as the device 10 is laid on its side against a generally horizontal surface 56. In particular, FIG. 7 illustrates the lid 22 as fluid is initially received and absorbed by the test strips 44 at the dipping ends 52. It will be appreciated that the dipping ends 52 are maintained in a lower, downward position when the device 10 is tilted. Since position stabilizer 33, shown in FIG. 6, keeps the device 10 from rolling, the stabilizer thus also keeps the dipping ends 52 in this lowermost, downward position to facilitate receipt of the fluid sample by virtue of gravity.

When testing is completed, the device 10 may be stored to an upright, non-reactive position such that the dipping ends 52 are no longer submerged in the sample fluid within the cup 20.

Figure 8:
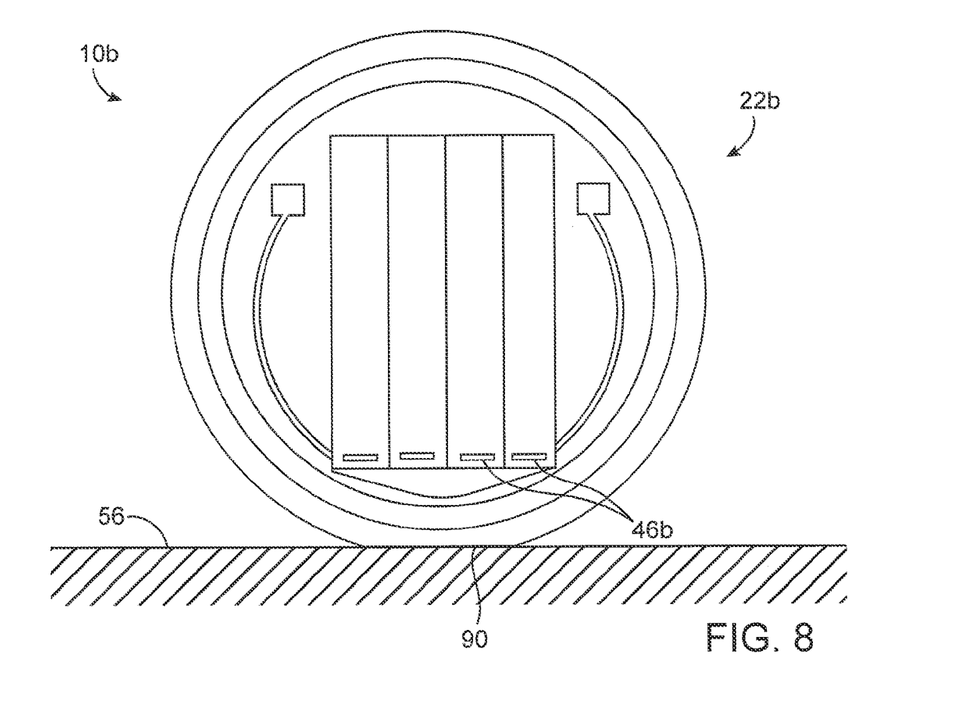
FIG. 8 is a front view of a second preferred embodiment of a fluid specimen collection device in a reactive position.

FIG. 8 is a front view of a second preferred embodiment of the device 10b where elements of similar structure are designated by the same reference numerals followed by the letter "b." In this embodiment 10b, the cup is similar to the first preferred embodiment 10 shown in FIGS. 1-7. The lid 22b also includes a position stabilizer 90 comprising a flat surface 90 located adjacent to the ports 46b and configured to align with the position stabilizer of the cup when the lid is locked to the cup such that both the position stabilizer of the cup and the lid position stabilizer 90 engage the generally horizontal surface 56.

Figure 9:
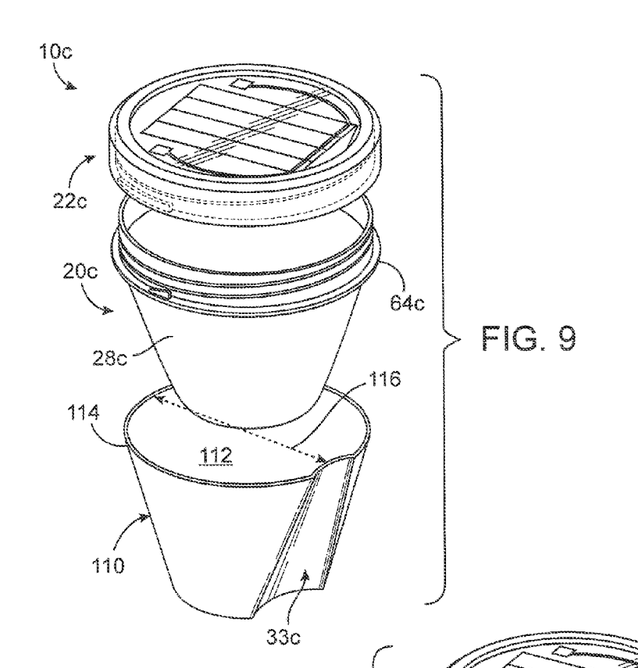
FIG. 9 is an exploded, perspective view of a third preferred embodiment of a fluid specimen collection device.

FIG. 9 illustrates a third preferred embodiment of the device 10c where elements of similar structure are designated by the same reference numerals followed by the letter "c." In this embodiment 10c, the lid 22c is substantially similar to the lid 22 in the first preferred embodiment shown in FIGS. 1-7. The cup 20c may comprise a generally cylindrical or conical sidewall 28c without any indentations. The position stabilizer 33c is preferably included in an add-on device 100 which, in this preferred embodiment, comprises a second outer cup 110 adapted to receive the cup 20c retaining the fluid. Thus, the cup 20c sits within or nests within the outer cup 110 comprising the position stabilizer 33c. The outer cup 110 must comprise an internal space 112 large enough, by width and depth, to receive the inner cup 20c such that flange 64c rests on the top edge 114 of the outer cup. The cross-dimension 116 of the outer cup 110 must be large enough to accommodate the inner cup 20c even with the indentation 33c.

Figure 10:
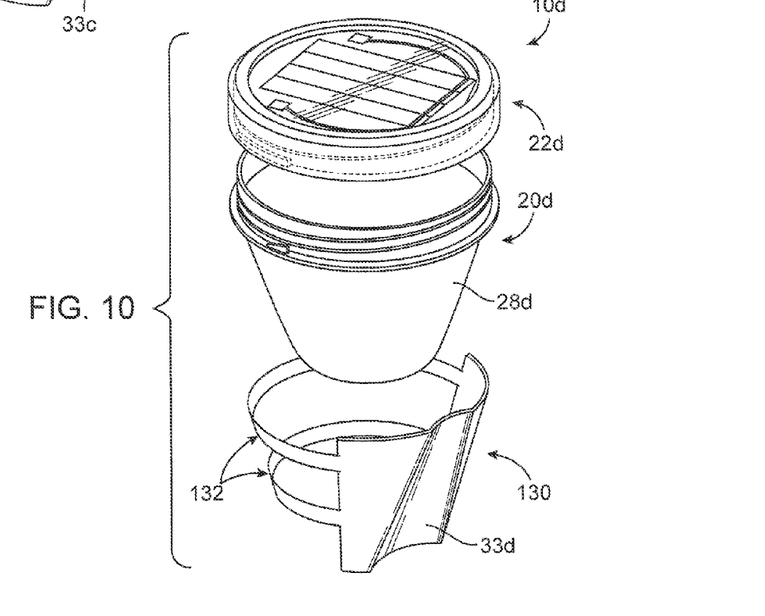
FIG. 10 is an exploded, perspective view of a fourth preferred embodiment of a fluid specimen collection device.

FIG. 10 illustrates a fourth preferred embodiment of the device 10d where elements of similar structure are designated by the same reference numerals followed by the letter "d." In this embodiment 10d, the lid 22d is substantially similar to the lid 22 in the first preferred embodiment shown in FIGS. 1-7. The cup 20d may comprise a generally cylindrical or conical sidewall 28d without any indentations. The position stabilizer 33d is included in a strap-on or add-on device 130, which in this preferred embodiment, comprises a sleeve or jacket 130 adapted to receive the cup 20c retaining the fluid. Thus, the jacket 130 comprises one or more wraparound bands, or arms, 132 configured to wrap around and secure the cup 20d.

It will be appreciated that the position stabilizer, namely, the indentation, 35 can be formed at a variety of angles with respect to the top planar surface of the lid 22. In the first preferred embodiment as shown in FIG. 6, the entire length of the indentation 35 need not abut the horizontal surface 56, although the stabilizer 33 could be configured to do so. Instead, in the first preferred embodiment, the cup 20 rests on a bottom portion 82 of the stabilizer 33 which abuts the surface 56 as shown in FIG. 6. The viewing angle of the device 10 when placed on its side may be varied by configuring the stabilizer.

Figure 11:
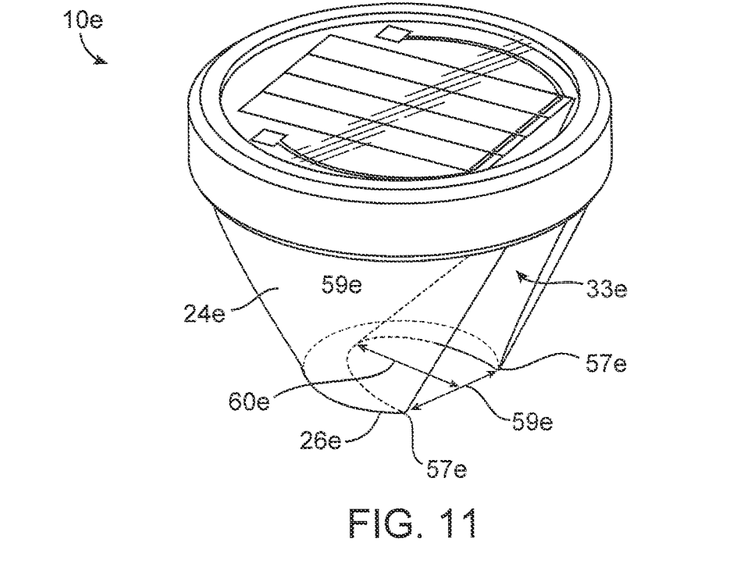
FIG. 11 is a perspective view of a fifth preferred embodiment of a fluid specimen collection device.

FIG. 11 illustrates a fifth preferred embodiment 10e where the indentation 33e extends deeper towards the reservoir 24e of the cup 20e, thereby further reducing internal volume requirements. Where the lowest points 57e of the ridges 39e of the indentation 33e define a line 58e extending therebetween, the bottom of the indentation 33e may comprise an innermost point 59e that is spaced an inward distance 60e from the line 58e in the preferred range of 0.5 inch to 3.5 inches in the fifth preferred embodiment. Such a deeper indentation 33e as shown in FIG. 11 reduces the internal volume requirements necessary for collection and testing. This will be appreciated by those providing samples who may not be able to produce a high volume of fluid. In this preferred embodiment, the indentation reduces internal volume preferably in the range of 4 ml to 14 ml than if the cup were configured without such an indentation.

Figure 12:
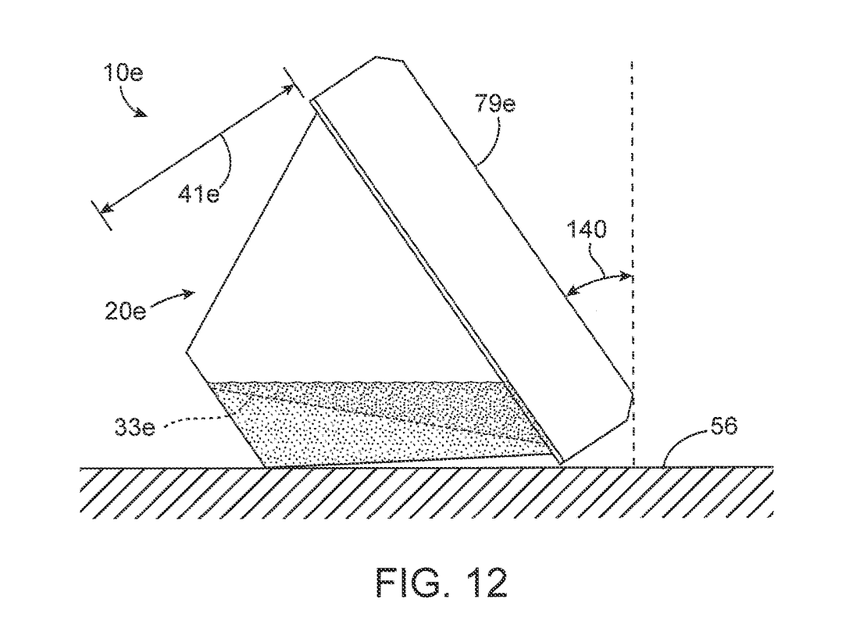
FIG. 12 is a side elevation view of the fifth preferred embodiment in a reactive position.

In FIG. 12, the fifth preferred embodiment 10e is configured to angle the top planar surface 79e of the lid 22e more upwardly, namely, at a greater angle 140 from a vertical axis "V" perpendicular to the horizontal surface 56. The higher angle 140 is also facilitated by a shorter cup height 41e as well as a cut bottom 26 having a shorter radius, thereby causing the cup 20e to face more upwardly when placed in the reactive position as shown. In this preferred embodiment, the height 142 of the cup 20e from the bottom up to where the cup meets the lid 22e is preferably less than 2 inches, and the radius of the cut bottom 26e is preferably less than 1 inch. This causes the top planar lid surface 79e to lie at a greater angle 140 from the vertical axis V, thereby making the test results more easily viewable from above.

Figure 13:
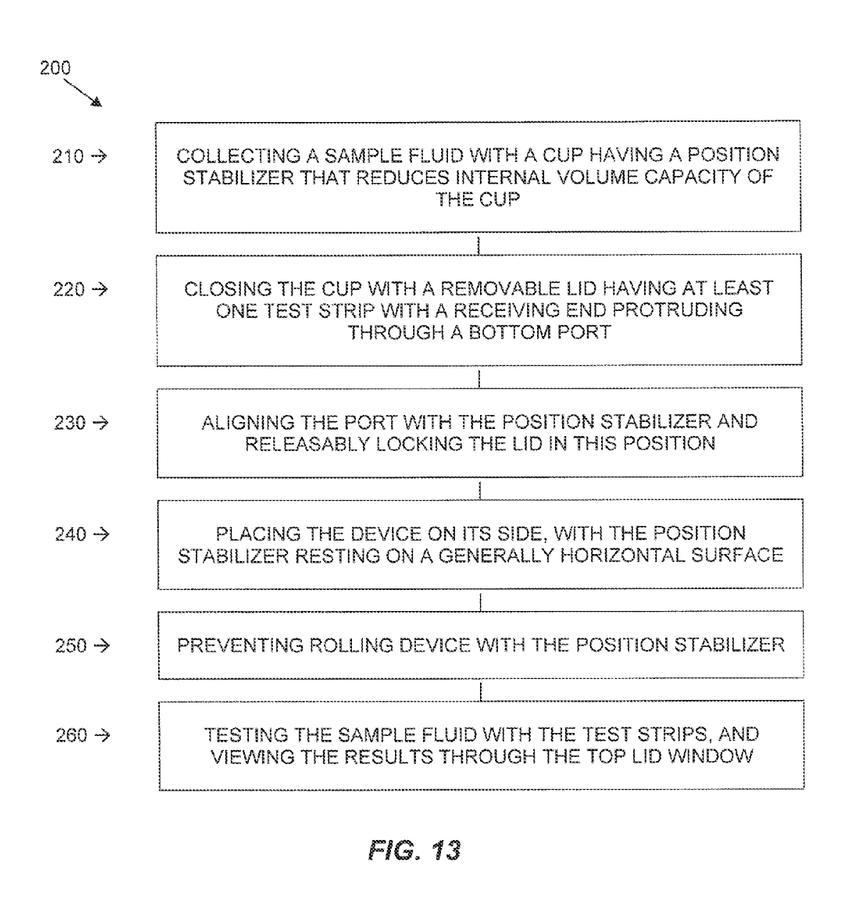
FIG. 13 illustrates a preferred method for collecting and testing a sample fluid for drugs and/or adulteration.

In FIG. 13, a preferred method 200 of collecting and testing a sample fluid for drugs and/or adulteration is provided. The method 200 comprises the step 210 of collecting a sample fluid with a cup having a position stabilizer. Step 220 comprises closing the cup with a removable lid having at least one test strip with a receiving end protruding through a bottom port. Step 230 comprises aligning the port with the position stabilizer and releasably locking the lid in this position.

Step 230 also comprises bringing the sample fluid into contact with the test strip(s) housed in the lid, particularly with the dipping portions exposed and protruding through the bottom ports of the lid aligned with the position stabilizer. Step 240 comprises placing the device on its side, with the position stabilizer resting on a generally horizontal surface. Step 240 also comprises angling the test results showing through the top surface of the lid upwardly by configuring the stabilizer in such a way Step 260 comprises testing the sample fluid with the test strips, and viewing the results through the top lid window.

Many alterations and modifications may be made by those having ordinary skill in the art without departing from the spirit and scope of the invention. Therefore, it must be understood that the illustrated embodiments have been set forth only for the purposes of examples and that they should not be taken as limiting the invention as defined by the following claims. For example, notwithstanding the fact that the elements of a claim are set forth below in a certain combination, it must be expressly understood that the invention includes other combinations of fewer, more or different elements, which are disclosed in above even when not initially claimed in such combinations.

The words used in this specification to describe the invention and its various embodiments are to be understood not only in the sense of their commonly defined meanings, but to include by special definition in this specification the generic structure, material or acts of which they represent a single species.

The definitions of the words or elements of the following claims are, therefore, defined in this specification to not only include the combination of elements which are literally set forth. In this sense it is therefore contemplated that an equivalent substitution of two or more elements may be made for any one of the elements in the claims below or that a single element may be substituted for two or more elements in a claim. Although elements may be described above as acting in certain combinations and even initially claimed as such, it is to be expressly understood that one or more elements from a claimed combination can in some cases be excised from the combination and that the claimed combination may be directed to a subcombination or variation of a subcombination.

Insubstantial changes from the claimed subject matter as viewed by a person with ordinary skill in the art, now known or later devised, are expressly contemplated as being equivalently within the scope of the claims. Therefore, obvious substitutions now or later known to one with ordinary skill in the art are defined to be within the scope of the defined elements.

The claims are thus to be understood to include what is specifically illustrated and described above, what is conceptionally equivalent, what can be obviously substituted and also what incorporates the essential idea of the invention.

What is claimed is:

1. A fluid collection device, comprising:
a cup defining a reservoir and comprising a top, a bottom, and a sidewall having a tapered position stabilizer, the position stabilizer comprising an indentation, the indentation forming first and second ridges adapted to abut, at least in part, a generally horizontal surface on which the device rests when tilted, where a first distance between the first and second ridges at the top of the cup is less than a second distance between the first and second ridges at a bottom of the cup, the indentation being configured to prevent the cup from rolling when the cup is tilted to rest the stabilizer against the generally horizontal surface; and
a lid removably coupled to the cup, the lid comprising a test strip and an opening accessible to the test strip, the lid being movable with respect to the cup from an unlocked position to a locked position, where the opening is located adjacent a tilt portion of a periphery of the lid and axially aligned with the position stabilizer;
wherein the lid is configured to be releasably locked in the locked position such that the tilt portion of the periphery of the lid is aligned with the position stabilizer to direct fluid within the cup towards the opening in the lid, wherein the indentation provides continuous fluid communication between the test strip and the reservoir.

2. The device of claim 1, wherein the indentation comprises a bottom width in the range of 0.75 to 1.5 inches and a top width in the range of 0.5 to 1.0 inch.

3. The device of claim 2, wherein:
each of the first and second ridges has a bottom point;
the pair of bottom points define a line extending therebetween; and
an innermost point of a bottom of the indentation extends an inward distance from the line in a range of 0.1 inch to 1 inch.

4. The device of claim 1, further comprising a releasable lock to temporarily lock the lid in the fixed position.

5. The device of claim 1, wherein the lid comprises a lid position stabilizer configured to align with the position stabilizer when the lid is locked to the cup.

6. The device of claim 5, wherein the lid position stabilizer comprises a flat surface formed in the tilt portion of the periphery.

7. A fluid collection device, comprising:
a cup comprising a top and a bottom configured to hold a sample fluid;
a position stabilizer configured to prevent the cup from rolling when the cup is tilted and resting on a generally horizontal surface, the position stabilizer comprising a tapered indentation running vertically along a sidewall from a lower portion adjacent to the bottom of the cup to a top portion adjacent to the top of the cup so as to form a pair of ridges configured to abut, at least in part, the generally horizontal surface, the pair of ridges separated a first distance at the top of the cup and the pair of ridges separated a second, greater distance at the bottom of the cup;
a lid removably coupled to the cup, the lid having a continuous, circular outer perimeter, the lid comprising a test strip and an opening accessible to the test strip the lid being movable with respect to the cup from an unlocked position to a locked position where the opening is accessible to the test strip in the locked position and the opening, in the locked position, is located adjacent a tilt portion of a periphery of the lid and axially aligned with the position stabilizer, wherein when the cup rests along the pair of ridges on the generally horizontal surface, the outer, upper surface of the lid forms an acute angle with a line touching the lid and perpendicular to the generally horizontal surface.

8. The device of claim 7, wherein the position stabilizer is integral with the cup.

9. The device of claim 7, wherein:
the cup comprises a first cup; and
the position stabilizer is included in a second outer cup configured to receive the first cup.

10. The device of claim 7, further comprising a releasable lock to temporarily lock the lid in a fixed position with respect to the cup where the opening in the lid is aligned with the position stabilizer to facilitate flow of fluid into the lid when the cup is tilted and stabilized by the groove.

11. The device of claim 7, wherein the cup comprises a reduced internal volume configured to require less than a full reservoir of fluid in order to direct a sufficient amount of said fluid to the lid.

12. The device of claim 7, wherein:
each ridge has a bottom point and a top point;
the pair of top points define a first distance therebetween in the range of 0.5 to 1.0 inch;
the pair of bottom points define a line extending therebetween having a distance in the range of 0.75 to 1.5 inches; and
an innermost point of a bottom of the indentation extends an inward distance from the line in a range of 0.1 inch to 1 inch.

13. The device of claim 12, wherein the bottom point of each ridge abuts the horizontal surface.

14. A fluid collection device, comprising:
a cup comprising a top and a bottom configured to hold a sample fluid;
a position stabilizer configured to prevent the cup from rolling when the cup is tilted and resting on a generally horizontal surface, the position stabilizer comprising a tapered indentation formed into a sidewall running vertically from a lower portion adjacent to the bottom of the cup to an upper portion adjacent to the top of the cup so as to form a pair of ridges that extend upwardly toward each other, the pair of ridges separated a first distance at the top of the cup and the pair of ridges separated a second, greater distance at the bottom of the cup;
a lid removably coupled to the cup, the lid comprising a test strip and an opening accessible to the test strip, the lid being movable with respect to the cup from an unlocked position to a locked position wherein the opening is located adjacent a tilt portion of a periphery of the lid and axially aligned with the position stabilizer,
wherein the lid is configured to be releasably locked in the locked position with respect to the cup so as to axially align the opening with the position stabilizer, wherein, when in either the locked position or unlocked position, the opening fluidly communicates with an interior of the cup.

15. The device of claim 14, wherein:
each ridge has a bottom point a top point;
the pair of top points define a first distance therebetween in the range of 0.5 to 1.0 inch;
the pair of bottom points define a line extending therebetween having a distance in the range of 0.75 to 1.5 inches; and
an innermost point of a bottom of the indentation extends an inward distance from the line in a range of 0.1 inch to 1 inch.

16. The device of claim 14, wherein the position stabilizer is integral with the cup.

17. The device of claim 14, wherein the position stabilizer is included in an add-on device.

\* \* \* \* \*